United States Patent

Magidson et al.

[11] Patent Number: 5,904,143
[45] Date of Patent: May 18, 1999

[54] FOAM EARPLUG WITH NON-PERMEABLE ELASTOMERIC COATING

[76] Inventors: Mark Magidson, 9000 Thrasher Ave., Los Angeles, Calif. 90069; Steve Young, 1565 W. 222nd St., Los Angeles, Calif. 90501

[21] Appl. No.: 08/734,206

[22] Filed: Oct. 21, 1996

[51] Int. Cl.⁶ ............................................. A61F 11/00
[52] U.S. Cl. ............................................. 128/864; 128/865
[58] Field of Search .................... 128/846, 864–866; 2/209, 428; 181/129, 130, 135

[56] References Cited

U.S. PATENT DOCUMENTS

| | | |
|---|---|---|
| 2,441,866 | 5/1948 | Cantor . |
| 2,446,707 | 8/1948 | Leight ............................ 128/864 |
| 2,672,863 | 2/1954 | Leight . |
| 2,785,676 | 3/1957 | Berkman . |
| 3,016,054 | 1/1962 | Rosenblatt . |
| 3,102,538 | 9/1963 | Cowan . |
| 3,154,171 | 10/1964 | Knutson et al. . |
| 3,535,710 | 10/1970 | Aileo . |
| 3,728,741 | 4/1973 | Lepor . |
| 3,771,521 | 11/1973 | Kittredge . |
| 3,872,559 | 3/1975 | Leight ............................ 128/867 |
| 3,881,570 | 5/1975 | Lewis ............................ 128/864 |
| 4,089,332 | 5/1978 | Rose . |
| 4,160,449 | 7/1979 | Wade . |
| 4,215,683 | 8/1980 | Lundin et al. . |
| 4,241,806 | 12/1980 | Metzger . |
| 4,340,129 | 7/1982 | Salyers . |
| 4,461,290 | 7/1984 | Gardner, Jr. et al. . |
| 4,480,715 | 11/1984 | Brooks . |
| 4,498,469 | 2/1985 | Csiki . |
| 4,594,278 | 6/1986 | Nixon . |
| 4,683,979 | 8/1987 | Ghibu et al. . |
| 4,774,938 | 10/1988 | Leight ............................ 128/864 |
| 4,808,465 | 2/1989 | Vane . |
| 4,818,603 | 4/1989 | Mueller . |
| 4,863,791 | 9/1989 | Steward et al. . |
| 4,940,112 | 7/1990 | O'Neill . |
| 5,023,955 | 6/1991 | Murphy, II et al. . |
| 5,058,705 | 10/1991 | Rheinlander . |
| 5,452,731 | 9/1995 | Dickman . |
| 5,459,291 | 10/1995 | Haines et al. . |
| 5,500,958 | 3/1996 | Falco . |

*Primary Examiner*—Michael A. Brown
*Attorney, Agent, or Firm*—Charles H Schwartz

[57] ABSTRACT

A foam earplug for reception at least partially within the ear canal, including a body portion formed of resilient foam plastic material. The foam material has an open cell structure, a size and shape for at least partial reception within the ear canal. The earplug has an outer thin coating of a non-permeable elastomeric material and with the coating forming a skin bonded on the body portion, non-permeable to air, at least in the area of the body portion received within the ear canal for providing an increase in attenuation of sound as compared with the attenuation of sound produced by resilient foam plastic material without the thin coating of the non-impermeable elastomeric material.

26 Claims, 2 Drawing Sheets

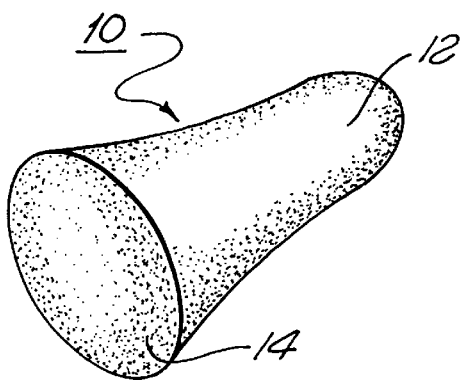
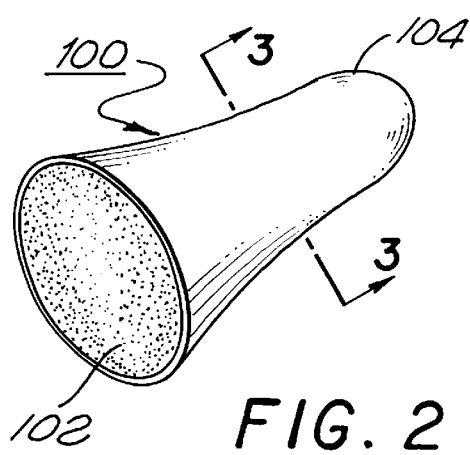
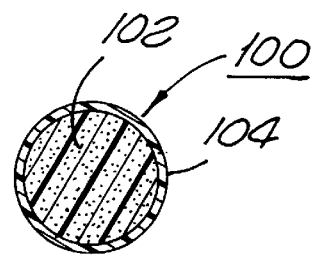
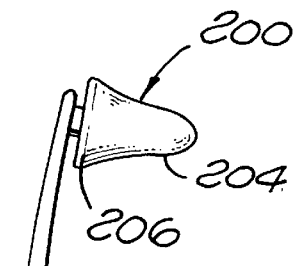
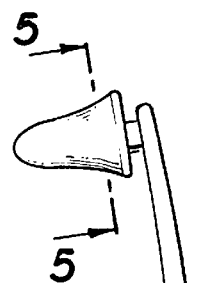
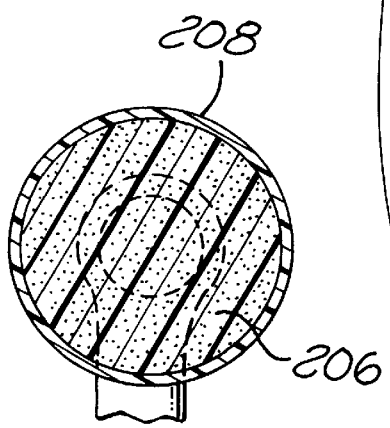
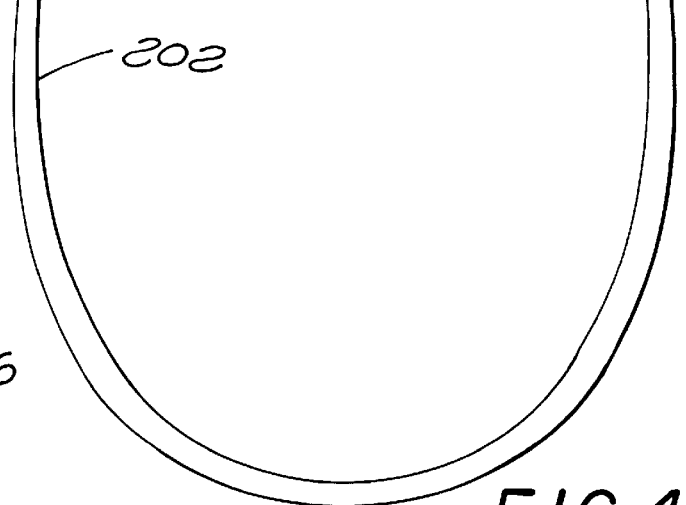

FOAM EARPLUG WITH NON-PERMEABLE ELASTOMERIC COATING

BACKGROUND OF THE INVENTION

The present invention relates to a foam earplug and more specifically to a foam earplug with a non-permeable elastomeric coating.

In the prior art, foam earplugs have been made of a slow recovery resilient foam material and such slow recovery earplugs have gained wide acceptance. As an example, an earplug as shown and described in U.S. Pat. No. RE29487 is used by rolling the earplug down to a small diameter and then inserting the rolled earplug into the ear. The earplug is then allowed to expand over a period of time, generally between a few seconds to as much as about a minute, to fill a substantial portion of the user's ear canal.

Slow recovery earplugs may be made by a variety of techniques. One method of manufacturing is to punch out cylindrical earplugs from a sheet of slow recovery material. A second method of manufacturing is to mold in a closed or open cavity mold earplugs in a desired shape. As an example, a molded earplug is shown in U.S. Pat. No. 4,774,938. This patent also demonstrates that a molded plug will typically have smaller cells at the surface of the earplug since the molding process would tend to compress the cells at the surface. Whether the earplug is formed by cutting out of a sheet or by molding within a cavity, the outer surface is porous and allows the escape of air.

In the prior art, there are also earplugs that have been designed that use a combination of an outer shell or bag and with some sort of sound absorbing material such as a foam or fibrous material maintained within the shell or bag. Examples of earplugs that have an outer relatively thick shell are shown by U.S. Pat. Nos. 4,461,290, 2,441,866 and 2,672,863. Examples of earplugs that have an outer bag are shown by U.S. Pat. Nos. 4,160,449, 3,771,521 and 4,498,469. Some of these patents have the inner sound absorbing material formed by a foam and some by fibrous material but in both cases the outer shell or bag is formed as a separate member and it does not have the characteristics of being a close intimate skin or coating bonded on the surface of the foam earplug.

SUMMARY OF THE INVENTION

The present invention provides for a foam earplug having a bonded non-permeable elastomeric outer coating. The earplug is formed of a body portion of resilient foam plastic material having a multiple open cell structure and having a size and shape for at least partial reception within the ear canal of the user. An outer coating of a non-permeable elastomeric material forms a bonded skin on the body portion which is non-permeable to air at least in the area of the body portion that is received in the ear canal of the user. This structure of a thin non-permeable elastomeric coating bonded to the outer surface of the foam earplug provides for a surprising increase in attenuation of sound as compared with the attenuation of sound produced by the same earplug, constructed from the same resilient foam plastic material, without the thin bonded coating of non-permeable elastomeric material.

As a first method of making the earplugs of the present invention, a mold which has at least one, but normally a multitude of cavities, is provided for molding individual earplugs. Prior to the insertion of foamable plastic material, each cavity is coated with the thin coating of non-permeable elastomeric material. The foamable plastic material is then inserted into the coated cavities and after fully foaming the earplugs are removed and have the thin coating of non-permeable material permanently bonded to the foamed earplug. As indicated above, this structure provides a very beneficial result in increasing sound attenuation. A second method of producing the earplug would be to mold the earplugs in the cavities or punch out from a sheet in the normal way. The individual earplugs then could be sprayed or dipped with the coating of non-permeable elastomeric material to bond to the surface of the earplug.

The earplug itself may be made of different types of foam and with one embodiment using a slow recovery foam. In this way, the earplug can be rolled down for insertion into the ear and then as the slow recovery earplug recovers its original shape it fills the ear canal and the non-permeable elastomeric coating is now in contact with the surface of the ear canal. When using such a slow recovery foam, the coating normally would not cover the back end of the plug so that air can escape out of a plug when it is rolled down prior to insertion. Air can then re-enter into the plug through the back end as the slow recovery foam recovers. If the earplug is a push-in type that does not have to be rolled down prior to use then the coating could cover the entire ear plug including the back end.

The non-permeable elastomeric coating could be made of a number of elastomeric materials including urethane, latex, etc. A specific material which provides the desired non-permeable elastomeric coating is referred to as an "aliphatic urethane lacquer" and has a Toluene solvent base and having the following physical characteristics:

| | |
|---|---|
| Solids by weight | 7–10% |
| Solids by volume | 5–8% |
| Tensile Strength | 5,500 PSI |
| Tear Strength | 500 PLI |
| Elongation | 350% |
| Viscosity, #2 Zahn | 14–17 sec. |
| Flash Point | 33–37 F |

This material may be used either as a pre-mold coating or a spray-top coat and is generally used to produce a protective coating on foam materials. Normal suggested uses are in the automotive field, exercise equipment field, office furniture field and toys or sporting goods. The prior art coating is generally thick enough to provide a protective surface that can be cleaned and would typically not be used as a very thin coating as present with the earplug of the present invention.

It should also be appreciated that the foam earplug of the present invention may take a variety of forms including typically earplugs that are rolled down and inserted into the ear as well as semi-aural devices. These are typically two ear protectors that are placed on opposite ends of a band which is constructed of plastic or metal. The band holds the ear protectors under tension partially within the ear canal, although not as deep as a typical earplug. Earplugs would normally have the highest noise reduction rating and the semi-aural headband devices would typically have a lower noise reduction rating. In either case, the use of the non-permeable elastomeric coating produces a significant improvement in increasing the attenuation to have a higher noise reduction rating as compared with similar devices without the coating.

Although the exact reason for this increase in attenuation is not known, it appears that there is a synergistic effect between the benefits of the foam material and the benefits of the thin non-permeable coating of elastomeric material. Various explanations have been postulated as to why the increase in the attenuation occurs. These explanations include 1) sound traveling through the open cell structure of the foam earplug which are not absorbed within the earplug, is blocked by the non-permeable coating, 2) sound that could leak through the open cell structure in contact with the ear canal is blocked by a more intimate contact of the non-permeable coating with the surface of the ear canal and 3) sound passing through the ear plug is blocked by the difference in materials forming a barrier layer where the coating and the foam earplug are bonded. In any event, the increase in attenuation is significant and may range (dependent upon frequency) between 1 to 4 or more db's higher than the attenuation level for devices without the coating.

A clearer understanding of the invention will be had with reference to the following description and drawings.

BRIEF DESCRIPTION OF THE DRAWINGS

FIG. 1 is an illustration of a foam earplug of the prior art;

FIG. 2 is an illustration of a coated foam earplug in accordance with the present invention;

FIG. 3 is a cross-sectional view of the earplug taken along lines 3—3 in FIG. 2;

FIG. 4 is an illustration of a semi-aural headband type of earplug using ear protectors in accordance with the present invention;

FIG. 5 is a cross-sectional view of an ear protectors taken along lines 5—5 of FIG. 4;

FIG. 1 illustrates a prior art earplug 10 typically molded from a slow recovery foam material. As can be seen, the earplug has a generally bullet-shape main body 12 with a flared outer end 14. This type of earplug would have the cells on the outer surface of the earplug typically being smaller at the outer surface and with larger cells in the center of the plug. In this type of molded foam earplug since the surface of the plug has smaller cells, a smoother configuration is generally formed on the outer cell surface than if the earplug were formed by cutting the earplug from a flat sheet. Although the earplug 10 may have smaller cells at the outer surface, the molded plugs are all porous on the outer surface although air may pass through the outer surface of the plug a little more slowly than through the larger cells in the center of the plug.

Figure 6:
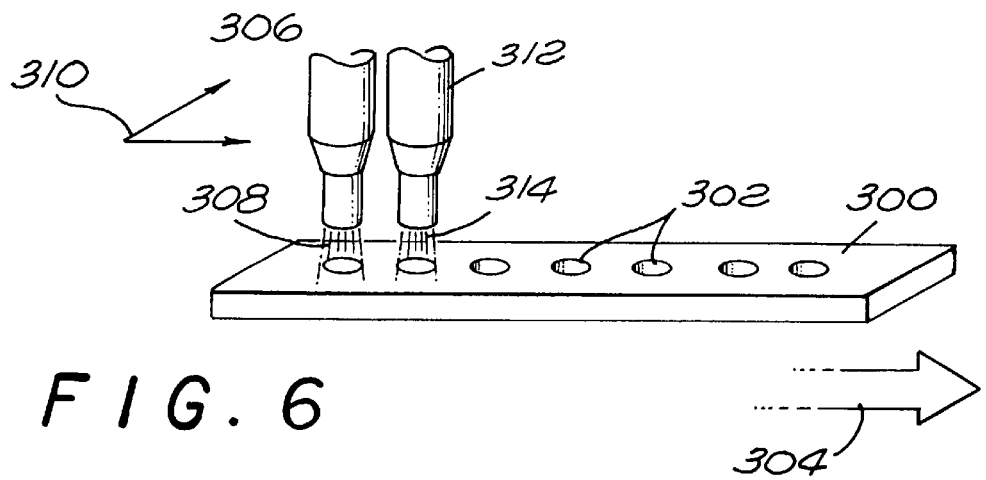
FIG. 6 is an illustration of a method of producing the earplug of the present invention including using coating.

A first embodiment of the present invention is illustrated in FIGS. 2 and 3. The present invention has a plug 100 which has an inner body 102 and an outer bonded coating or skin 104. The earplug 100 has generally the same shape as the prior art earplug in having a bullet shape main body portion with a flared back end. The inner body 102 may be constructed of the slow recovery foam or other types of resilient foams and the outer coating may be formed of a variety of non-permeable elastomeric materials including urethane, latex, etc.

As indicated above, a suitable material is described as an aliphatic urethane lacquer and has the following physical characteristics:

| | |
|---|---|
| Solids by weight | 7–10% |
| Solids by volume | 5–8% |
| Tensile Strength | 5,500 PSI |
| Tear Strength | 500 PLI |
| Elongation | 350% |
| Viscosity, #2 Zahn | 14–17 sec. |
| Flash Point | 33–37 F |

Other suitable non-permeable elastomeric coatings may also be used. The coating forms a thin skin which is intimately bonded to the foam earplug itself and may generally have a thickness between 0.1 to 35 mils. A preferred thickness would typically be 3 to 4 mils.

By producing earplugs with the non-permeable elastomeric coating as shown in FIGS. 2 and 3, it has been demonstrated that an increase of 1 to 4 or more dbs (dependent upon frequency) in attenuation over the same earplug composed only of foam material. This increase is significant considering the thin nature of the coating of the non-permeable elastomeric material. As indicated above, it is not clear as to the exact reason for this increase in attenuation but a number of possible explanations have been described above. Again, it is believed that there is some synergistic effect between the benefits of the foam material and the benefits of the thin non-permeable bonded layer of elastomeric material.

In addition to the form of the invention shown in FIGS. 2 and 3 it is also possible to have ear protectors, such as ear protectors 200, located at the ends of a headband 202 as shown in FIG. 4. This type of device provides for the ear protectors 200 to be partially inserted into the ear canal and to be held in the ear canal by the tension of the band 202. The band 202 may be constructed either of plastic or metal. As can be seen, the ear protectors 200 generally have a smaller insertable end 204 and a larger back portion 206 which typically would seal around the exterior of the opening to the ear canal.

FIG. 5 is a cross-sectional view of one of the ear protectors taken along lines 5—5 of FIG. 4 and as can be seen, the ear protector is made of an interior foam material 206 with an outer bonded coating of a non-permeable elastomeric material 208. Again, the elastomeric material may be any type of non-permeable material such as urethane, latex, etc. and may be the material described above as an aliphatic urethane lacquer.

The production of the earplug of the present invention may be produced by methods described with reference to FIGS. 6 to 8. In FIG. 6, a mold member 300 is shown to have multiple cavities 302, each having the form of an earplug or ear protector, shown in FIGS. 2 or 4. Using the earplug shown in FIG. 2 as an example, the cavity would have a general bullet shape with a flared outer end. The cavity mold 300 is then moved as shown by the arrow 304 and with a first spray member 306 applying a pre-mold coating of non-permeable elastomeric material 308 to the interior of each cavity 302. The spray head 306 may be actuated intermittently to ensure each cavity is coated with material 308 and without providing excess material to the exterior of the mold 300.

After each cavity 302 is coated with the non-permeable elastomeric material 308 an injector nozzle 312 fills each cavity with foamable plastic material 314 to form the main body of the earplug. After the foamable plastic material is completely foamed then the earplugs may be removed in the normal manner to produce the earplug as shown in FIG. 2. If it is desired to have the ends of earplugs also coated with the non-permeable elastomeric coating then the ends may be coated in a second step. This can be accomplished using the spray nozzle 306 before the earplugs are removed from the cavity or after the earplugs are removed from the cavities as shown in FIG. 8

Figure 7:
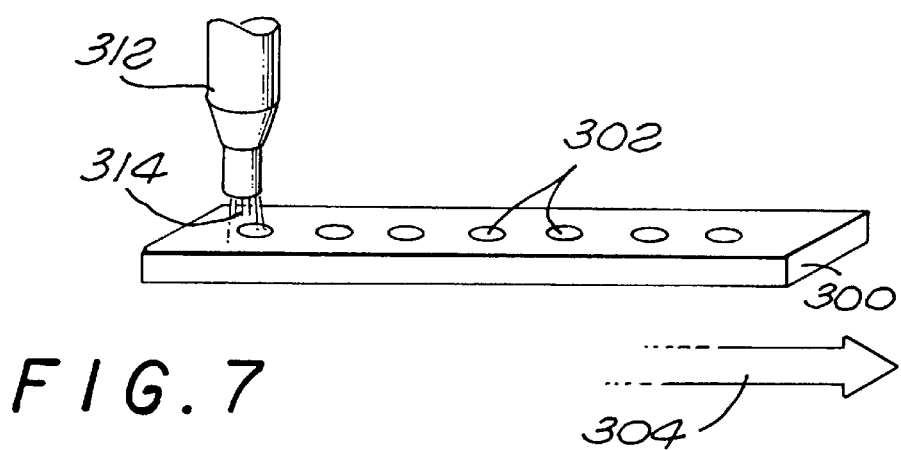
FIG. 7 is an illustration of a first step of a method of making an earplug of the present invention using a spray top-coat coating.
Figure 8:
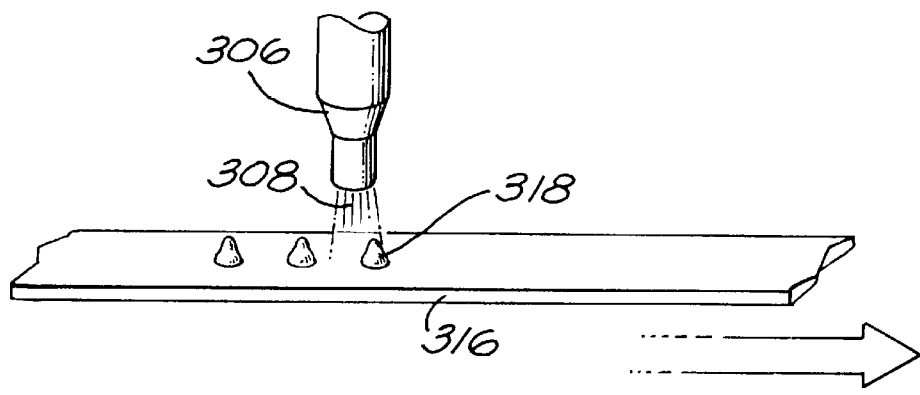
FIG. 8 is an illustration of a step of providing a spray top-coat coating which either completes the method of FIG. 7 or may provide an additional step for the method of FIG. 6.

In a second method of production shown in FIG. 7, the same cavity molds 300 having the plurality of cavities 302 is used and with the injection or nozzle 312 supplying foamable plastic material 314 to the interior of the cavities After the foamable plastic material has fully foamed, earplugs 318 are removed and may then be placed on a conveyer belt 316 shown in FIG. 8. The individual earplugs 318 are then sprayed using the sprayer head 306 with the non-permeable elastomeric material 308 to top coat the earplugs 318 with the coating.

The resultant earplug therefore has a body portion formed of resilient foam plastic material and an outer thin coating of a non-permeable elastomeric material to form the skin bonded on the body portion and with the combination having attenuation greater than the attenuation of an earplug formed only of the molded resilient foam plastic material. The thickness of the coating of non-permeable elastomeric material may have a thickness in the range of 0.1 to 35 mils and with a preferred thickness of about 3 to 4 mils.

Although the invention has been described with reference to particular embodiments, it is to be appreciated that various adaptations and modifications may be made and the invention is only to be limited by the appended claims.

We claim:

1. A foam earplug for reception at least partially within the ear canal, including, a body portion formed of resilient foam plastic material having a multiple open cell structure and having a size and shape for at least partial reception within the ear canal, and an outer thin coating of a non-permeable elastomeric material different than the material forming the body portion and with the coating forming a skin bonded on the body portion, non-permeable to air, at least in the area of the body portion received within the ear canal for providing an increase in attenuation of sound as compared with the attenuation of sound produced by the resilient foam plastic material without the thin coating of the non-impermeable elastomeric material.

2. The earplug of claim 1 wherein the resilient foam plastic material is a slow recovery material and the skin, formed by the thin coating, does not cover the body portion in an area external to the body portion received within the ear canal to allow for air to escape when the earplug is rolled down for insertion in the ear canal and to subsequently recover when in the ear canal.

3. The earplug of claim 1 wherein the skin formed by the thin coating covers the entire body portion to prevent air to escape when the earplug is inserted within the ear canal.

4. The earplug of claim 1 wherein the body portion has a size and shape to be received substantially within exterior and interior portions of the ear canal.

5. The earplug of claim 1 wherein the body portion has a size and shape to be received only within an exterior portion of the ear canal.

6. The earplug of claim 1 wherein the outer thin coating of non-permeable elastomeric material is a material defined as an aliphatic urethane lacquer.

7. The earplug of claim 1 wherein the outer thin coating of non-permeable elastomeric material has a thickness in the range of 0.01 to 35 mils.

8. The earplug of claim 1 wherein the outer thin coating of non-permeable elastomeric material has a thickness of about 3 to 4 mils.

9. A method of making a foam earplug having a thin skin of a non-permeable elastomeric material, including the following steps:

providing a mold having at least one cavity to form an earplug having a size and shape to fit at least partially within an ear canal, providing a non-permeable elastomeric material, coating the interior of the cavity with the non-permeable elastomeric material to form a thin skin on the interior of the cavity, providing a foamable plastic material, and placing the foamable plastic material within the coated cavity to foam to the size and shape of the cavity to form a resilient foam plastic earplug having a bonded thin skin of non-permeable elastomeric material.

10. The method of claim 9 wherein the foamable plastic material is provided to be a slow recovery foamable material.

11. The method of claim 9 including the additional steps of removing the coated earplug from the cavity and coating any portions of the earplug not coated by the non-permeable elastomeric material with additional non-permeable elastomeric material to form an earplug having its entire outer surface coated.

12. The method of claim 9 wherein the cavity is provided with a size and shape to produce an earplug to be received substantially within exterior and interior portions of the ear canal.

13. The method of claim 9 wherein the cavity is provided with a size and shape to produce an earplug to be received only within an exterior portion of the ear canal.

14. The method of claim 9 wherein the non-permeable elastomeric material is provided to be a material defined as an aliphatic urethane lacquer.

15. The method of claim 9 wherein the coating of non-permeable elastomeric material is to a thickness in the range of 0.01 to 35 mils.

16. The method of claim 9 wherein the coating of non-permeable elastomeric material is to a thickness of about 3 to 4 mils.

17. The method of claim 9 wherein the coating is applied by spraying.

18. A method of making a foam earplug having a thin skin of a non-permeable elastomeric material, including the following steps:

providing a mold having at least one cavity to form an earplug having a size and shape to fit at least partially within an ear canal, providing a foamable plastic material, and placing the foamable plastic material within the coated cavity to foam to the size and shape of the cavity to form a resilient foam plastic earplug, removing the earplug from the cavity, providing a non-permeable elastomeric material, coating the earplug with the non-permeable elastomeric material to bond a thin skin on the exterior of the earplug of non-permeable elastomeric material.

19. The method of claim 18 wherein the foamable plastic material is provided to be a slow recovery foamable material.

20. The method of claim 18 including the additional steps of coating the earplug with non-permeable elastomeric material to form an earplug having its entire outer surface coated.

21. The method of claim 18 wherein the cavity is provided with a size and shape to produce an earplug to be received substantially within exterior and interior portions of the ear canal.

22. The method of claim 18 wherein the cavity is provided with a size and shape to produce an earplug to be received only within an exterior portion of the ear canal.

23. The method of claim 18 wherein the non-permeable elastomeric material is provided to be a material defined as an aliphatic urethane lacquer.

24. The method of claim 18 wherein the coating of non-permeable elastomeric material is to a thickness in the range of 0.1 to 35 mils.

25. The method of claim 18 wherein the coating of non-permeable elastomeric material is to a thickness of about 3 to 4 mils.

26. The method of claim 18 wherein the coating is applied by spraying.

* * * * *